United States Patent [19]

Agee

[11] Patent Number: 4,833,170

[45] Date of Patent: May 23, 1989

[54] PROCESS AND APPARATUS FOR THE PRODUCTION OF HEAVIER HYDROCARBONS FROM GASEOUS LIGHT HYDROCARBONS

[75] Inventor: Kenneth L. Agee, Broken Arrow, Okla.

[73] Assignee: GTG, Inc., Broken Arrow, Okla.

[21] Appl. No.: 152,878

[22] Filed: Feb. 5, 1988

[51] Int. Cl.$^4$ ................................. C07G 1/04
[52] U.S. Cl. ...................... 518/703; 518/704; 252/373; 252/374
[58] Field of Search .................. 518/703, 704

[56] References Cited

U.S. PATENT DOCUMENTS

| | | | |
|---|---|---|---|
| 2,552,308 | 5/1951 | Buchmann et al. | 260/449.6 |
| 2,683,121 | 7/1954 | Vincent | 252/373 |
| 2,686,195 | 8/1954 | McAdams et al. | 260/449.6 |
| 3,549,335 | 12/1970 | Grotz, Jr. | 23/288 |
| 3,888,043 | 6/1975 | Child et al. | 48/197 R |
| 4,074,981 | 2/1978 | Slater | 48/197 R |
| 4,315,900 | 2/1982 | Nozawa et al. | 423/359 |
| 4,579,985 | 4/1986 | Minderhoud et al. | 585/310 |
| 4,579,986 | 4/1986 | Sie | 585/324 |
| 4,587,008 | 5/1986 | Minderhoud et al. | 208/109 |
| 4,640,766 | 2/1987 | Post et al. | 208/111 |

Primary Examiner—Howard T. Mars
Attorney, Agent, or Firm—Laney, Dougherty, Hessin & Beavers

[57] ABSTRACT

A process and apparatus for the production of heavier hydrocarbons from one or more gaseous light hydrocarbons is provided. The process comprises reacting the gaseous light hydrocarbons by autothermal reforming with air in the presence of recycled carbon dioxide and steam to produce a synthesis gas stream containing hydrogen and carbon monoxide. The synthesis gas stream is reacted in the presence of a hydrocarbon synthesis catalyst containing cobalt to form heavier hydrocarbons and water from the hydrogen and carbon monoxide. The heavier hydrocarbons and water are separated, and the resulting residue gas stream is subjected to catalytic combustion with additional air to form a product stream comprising carbon dioxide and nitrogen. The carbon dioxide is separated from the nitrogen to produce a nitrogen product stream, and at least a portion of the separated carbon dioxide is recycled to the autothermal reforming step.

20 Claims, 1 Drawing Sheet

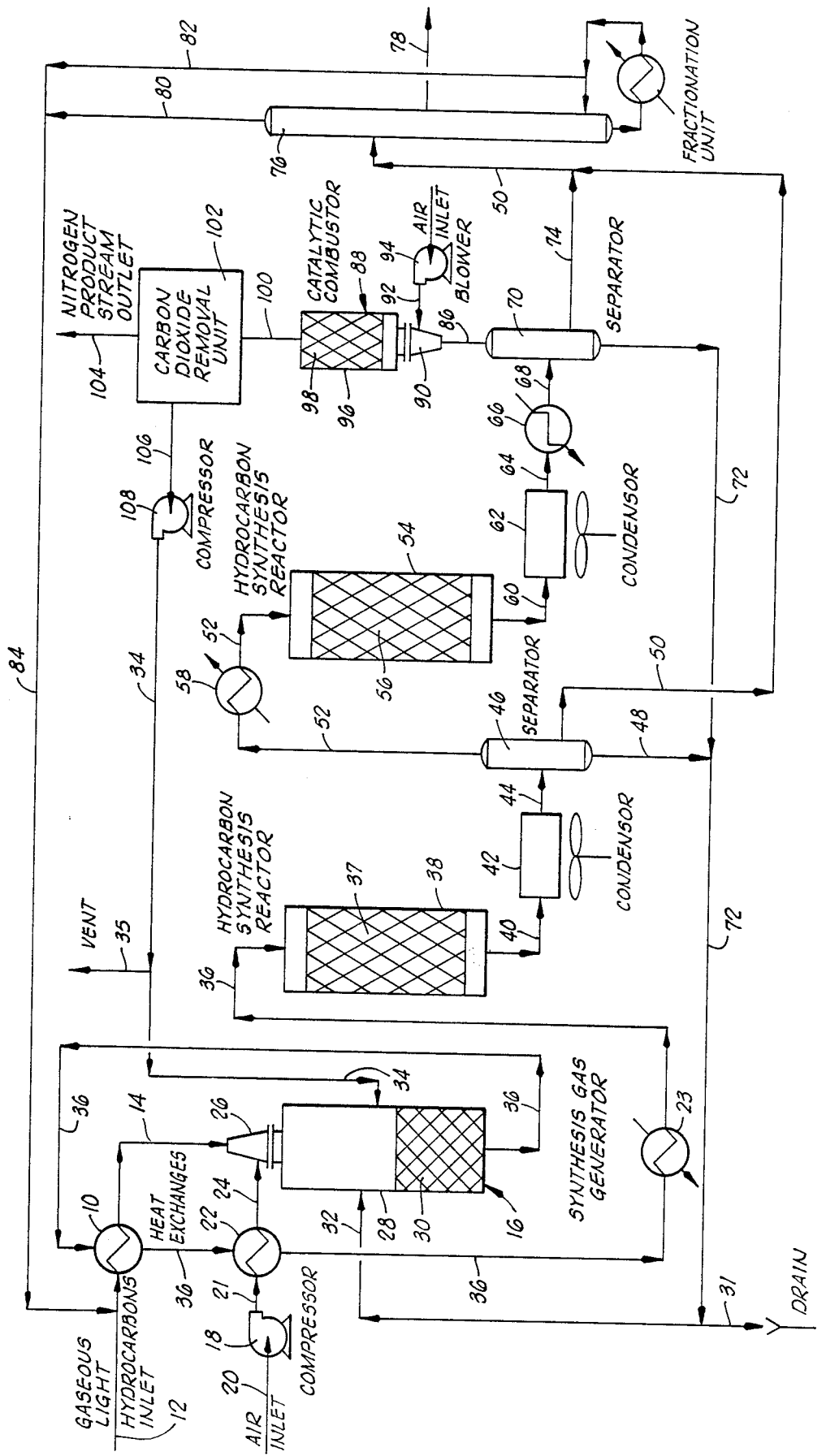

PROCESS AND APPARATUS FOR THE PRODUCTION OF HEAVIER HYDROCARBONS FROM GASEOUS LIGHT HYDROCARBONS

BACKGROUND OF THE INVENTION

1. Field of the Invention

The present invention relates to an improved process for the production of heavier hydrocarbons which combines autothermal reforming with air and the Fischer-Tropsch hydrocarbon synthesis reaction.

2. Description of the Prior Art

The synthetic production of hydrocarbons by the catalytic reaction of carbon monoxide and hydrogen is well known and is generally referred to as the Fischer-Tropsch reaction. Numerous catalysts have been used in carrying out the reaction, and at relatively low pressures (near atmospheric to 100 psig) and temperatures in the range of from about 300° F. to 600° F., both saturated and unsaturated hydrocarbons can be produced. The synthesis reaction is very exothermic and temperature sensitive whereby temperature control is required to maintain a desired hydrocarbon product selectivity. The Fischer-Tropsch reaction can be characterized by the following general reaction:

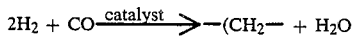

Two basic methods have been employed heretofore for producing the synthesis gas utilized as feedstock in the Fischer-Tropsch reaction. They are steam reforming wherein one or more light hydrocarbons such as methane are reacted with steam over a catalyst to form carbon monoxide and hydrogen, and partial oxidation wherein one or more light hydrocarbons are combusted sub-stoichiometrically to produce synthesis gas.

The basic steam reforming reaction of methane is represented by the following formula:

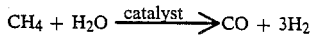

The steam reforming reaction is endothermic and catalyst containing nickel is often utilized. The hydrogen to carbon monoxide ratio of the synthesis gas produced by steam reforming of methane is approximately 3:1.

Partial oxidation is the non-catalytic, sub-stoichiometric combustion of light hydrocarbons such as methane to produce the synthesis gas. The basic reaction is represented as follows:

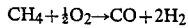

The partial oxidation reaction is typically carried out using high purity oxygen which involves high costs. The hydrogen to carbon monoxide ratio of synthesis gas produced by the partial oxidation of methane is approximately 2:1.

A combination of partial oxidation and steam reforming, known as autothermal reforming, wherein air is used as a source of oxygen for the partial oxidation reaction has also been used for producing synthesis gas heretofore. For example, U.S. Pat. Nos. 2,552,308 and 2,686,195 disclose low pressure hyrocarbon synthesis processes wherein autothermal reforming with air is utilized to produce synthesis gas for the Fischer-Tropsch reaction. Autothermal reforming is a simple combination of partial oxidation and steam reforming where the exothermic heat of the partial oxidation supplies the necessary heat for the endothermic steam reforming reaction. The autothermal reforming process can be carried out in a relatively inexpensive refractory lined carbon steel vessel whereby low cost is involved.

The autothermal process results in a lower hydrogen to carbon monoxide ratio in the synthesis gas than does steam reforming alone. That is, as stated above, the steam reforming reaction with methane results in a ratio of about 3:1 while the partial oxidation of methane results in a ratio of about 2:1. The optimum ratio for the hydrocarbon synthesis reaction carried out at low pressure over a cobalt catalyst is 2:1. When the feed to the autothermal reforming process is a mixture of light hydrocarbons such as a natural gas stream, some form of additional control is required to maintain the ratio of hydrogen to carbon monoxide in the synthesis gas at the optimum ratio of about 2:1.

By the present invention, an improved process for the production of heavier hydrocarbons from one or more light hydrocarbons using a combination of autothermal reforming synthesis gas production with air and Fischer-Tropsch hydrocabbon synthesis is provided wherein the ratio of hydrogen to carbon monoxide in the synthesis gas is more efficiently controlled near the optimum ratio, and a nitrogen product stream is produced in addition to the heavier hydrocarbon product.

SUMMARY OF THE INVENTION

A process for the production of heavier hydrocarbons from one or more gaseous light hydrocarbons is provided. The gaseous light hydrocarbons are combusted with air to partially oxidize a portion thereof and produce a gas stream comprising nitrogen and unreacted light hydrocarbons, hydrogen and carbon monoxide. The combustion gas stream is reacted with steam and carbon dioxide in the presence of a steam reforming catalyst to convert a substantial additional portion of the unreacted light hydrocarbons therein to hydrogen and carbon monoxide, and to produce a synthesis gas stream containing hydrogen and carbon monoxide in desired proportion. The synthesis gas stream is next reacted in the presence of a hydrocarbon synthesis catalyst containing cobalt to form heavier hydrocarbons and water from the hydrogen and carbon monoxide in the synthesis gas. The heavier hydrocarbons and water are separated from the hydrocarbon product stream leaving a residue gas stream comprising nitrogen and unreacted hydrogen, carbon monoxide, light hydrocarbons and carbon dioxide. The residue gas stream is subjected to catalytic combustion with additional air to react the oxidizable components therein and form an oxidized product stream comprising carbon dioxide, water vapor and nitrogen. Carbon dioxide is separated from the oxidized stream producing a nitrogen product stream, and at least a portion of the separated carbon dioxide is utilized in the initial production of synthesis gas to control the proportions of hydrogen and carbon monoxide therein and to recycle the carbon in the carbon dioxide.

The autothermal reforming process which is comprised of the first two steps recited above, i.e., the steps of combusting the gaseous light hydrocarbons with air to partially oxidize a portion thereof followed by reacting the combustion gas stream with steam and carbon dioxide in the presence of a steam reforming catalyst are carried out at a pressure in the range of from near atmospheric to about 100 psig and a temperature in the range of from about 1500° F. to about 3500° F. The Fischer-Tropsch hydrocarbon synthesis reaction is preferably carried out at substantially the same pressure as the autothermal reforming steps and at a temperature in the range of from about 350° F. to about 550° F. utilizing a catalyst containing cobalt.

As stated above, the hydrocarbon synthesis reaction is most efficient using a synthesis gas having a hydrogen to carbon monoxide ratio of about 2:1. The initial partial oxidation reaction produces the desired 2:1 ratio when the feed is methane, but typical feed streams such as natural gas contain varying amounts of other hydrocarbons, e.g., ethane and propane, which cause the overall hydrogen to carbon monoxide ratio in the product synthesis gas to be less than 2:1 when the feed stream is subjected to partial oxidation. However, the subsequent steam reforming step produces a higher hydrogen to carbon monoxide ratio which offsets and usually exceeds the lower ratio from the partial oxidation. Thus, one means of controlling the net hydrogen to carbon monoxide ratio is provided by the use of both partial oxidation and steam reforming, i.e., autothermal reforming. That is, the rate of steam fed to the reforming reaction can be varied to control the hydrogen to carbon monoxide ratio.

The use of autothermal reforming with air as the oxidizing agent provides several other benefits over prior art processes using partial oxidation alone, steam reforming alone or autothermal reforming with pure oxygen. For example, the autothermal technique which uses steam reforming for part of the synthesis gas conversion reduces the amount of oxygen or air required as compared to partial oxidation alone and reduces compression costs. Steam for the reforming reaction can be derived from byproduct water produced in the overall process of the invention. Utilizing air for the partial oxidation step clearly results in a significant reduction in cost as compared to utilizing pure oxygen. The partial oxidation and steam reforming reactions of the autothermal reforming technique can be carried out in a single reactor containing a bed of steam reforming catalyst. The use of air is also beneficial to the overall process of this invention in that nitrogen is produced in the synthesis gas stream which acts as a diluent in the subsequent hydrocarbon synthesis reaction. This is beneficial in that it results in fewer hot spots being formed on the catalyst surface and allows the reaction to be carried out at a higher temperature which in turn increases reaction rates and conversion efficiency.

The catalytic combustion of the residue gas stream after separation of synthetic heavier hydrocarbons and water therefrom produces a stream comprising carbon dioxide, water vapor and nitrogen. The carbon dioxide and water vapor are separated from the stream thereby producing a nitrogen product stream which can add revenue to the overall process. More importantly, the separated carbon dioxide is recycled to the steam reforming step whereby it reacts with additional unreacted light hydrocarbons to form additional hydrogen and carbon monoxide. This reaction is represented with methane as follows:

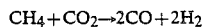
$$CH_4 + CO_2 \rightarrow 2CO + 2H_2$$

As indicated above, the reaction of the carbon dioxide with methane produces hydrogen and carbon dioxide in a ratio of 1:1 which provides an additional means for controlling the overall proportion of hydrogen to carbon monoxide in the synthesis gas stream produced. That is, in addition to the rate of steam introduced into the autothermal reforming reactor, the rate of carbon dioxide introduced thereinto can be varied to control the ratio of hydrogen to carbon monoxide in the synthesis gas.

Apparatus for carrying out the improved process of this invention is also provided by the invention.

It is, therefore, a general object of the present invention to provide an improved process and apparatus for the production of heavier hydrocarbons from one or more gaseous light hydrocarbons.

A further object of the present invention is the provision of a process and apparatus for the production of heavier hydrocarbons from a gaseous light hydrocarbon feed stream, such as a natural gas feed stream, wherein a nitrogen product stream is produced and the operating and capital costs of the process and apparatus are comparatively low.

Other and further objects, features and advantages of the present invention will be readily apparent to those skilled in the art upon a reading of the description of preferred embodiments which follows when taken in conjunction with the accompanying drawing.

BRIEF DESCRIPTION OF THE DRAWING

The drawing is a schematic representation of the process flow and apparatus of the present invention.

DESCRIPTION OF PREFERRED EMBODIMENTS

Referring now to the drawing, a continuous stream of gaseous light hydrocarbons, e.g., a natural gas stream, is conducted to a heat exchanger 10 by a conduit 12. While flowing through the heat exchanger 10, the stream of light hydrocarbons is heated by exchange of heat with a process stream of generated synthesis gas. Typically, the feed stream of light hydrocarbons is at a pressure in the range of from near atmospheric pressure to 100 psig and is preheated in the heat exchagger 10 to a temperature in the range of from about 500° F. to about 1000° F. From the heat exchanger 10, the preheated feed stream is conducted by a conduit 14 to a synthesis gas generator, generally designated by the numeral 16.

Air is drawn to an airccompressor 18 by way of an inlet conduit 20, and from the compressor 18, a stream of air is conducted to a heat exchanger 22 by a conduit 21. The stream of air is preheated in the heat exchanger 22 to a temperature in the range of from about 500° F. to about 1000° F. by exchange of heat with the synthesis gas stream exiting the heat exchanger 10. From the heat exchanger 22, the preheated air is conducted to the synthesis gas generator 16 by a conduit 24.

While the synthesis gas generator 16 can take various forms, it generally includes a burner 26 connected to one end of a reactor vessel 28. A bed of steam reforming catalyst 30 preferably containing nickel is disposed within the reactor 28 at the end opposite the burner 26.

The reactor 28 is preferably a refractory lined carbon steel vessel. Water, which instantly converts to steam, is introduced into the reactor 28 by way of a conduit 32 connected thereto, and carbon dioxide is introduced into the reactor 28 by way of a conduit 34 connected thereto.

In the operation of the synthesis gas generator 16, the pre-heated feed stream of gaseous light hydrocarbons is intimately mixed with a preheated stream of air in the burner 26 and ignited whereby the combustion reaction takes place within the reactor 28. The combustion reaction is carried out at a temperature in the range of from about 2000° F. to about 3000° F. under sub-stoichiometric conditions whereby the light hydrocarbons are partially oxidized, and a gas stream comprising nitrogen, unreacted light hydrocarbons, hydrogen and carbon monoxide is produced.

The unreacted light hydrocarbons in the combustion gas stream react with steam introduced into the reactor 28 in the presence of the reforming catalyst whereby additional hydrogen and carbon monoxide are produced therefrom. Simultaneously, carbon dioxide introduced into the reactor 28 reacts with unreacted light hydrocarbons to produce additional carbon monoxide and hydrogen. The resulting synthesis gas stream generated within the generator 16 is comprised of hydrogen, carbon monoxide, nitrogen and unreacted light hydrocarbons and exits the reactor 28 by way of a conduit 36.

In order to control the ratio of hydrogen to carbon monoxide in the synthesis gas stream produced in the synthesis gas generator 16 at a ratio as close to 2:1 as possible, the rates of water introduced into the reactor 28 by way of the conduit 32 and carbon dioxide introduced by way of the conduit 34 are varied. That is, the ratio of hydrogen to carbon monoxide in the produced synthesis gas stream, or the composition of the feed light hydrocarbon stream, or both, are monitored and used as the basis for changing the flow rates of steam and carbon dioxide to the reactor 28 whereby a constant ratio of hydrogen to carbon monoxide at about 2:1 is maintained.

The synthesis gas product stream produced in the generator 16 is conducted by the conduit 36 through the heat exchanger 10, then through the heat exchanger 22 and then to the inlet connection of a first hydrocarbon synthesis reactor 38. Upon exiting the generator 16, the synthesis gas is at a temperature in the range of from about 1000° F. to about 2000° F. As the synthesis gas stream flows through the heat exchanger 10 it gives up heat to the feed light hydrocarbon stream whereby the hydrocarbon stream is preheated to a temperature in the range of from about 500° F. to about 1000° F. In a like manner, as the synthesis gas stream flows through the heat exchanger 22, it gives up heat to the air flowing to the generator 16 whereby the air is also preheated to a temperature in the range of from about 500° F. to about 1000° F. Additional cooling of the synthesis gas stream is provided by a cooler or heat exchanger 35 disposed in the conduit 36 whereby the temperature of the synthesis gas entering the reactor 38 is in the range of from about 350° F. to about 550° F.

The hydrocarbon synthesis reactor 38 can take various forms, but preferably is a tubular reactor containing a fixed bed 37 of hydrocarbon synthesis catalyst. The catalyst is preferably comprised of cobalt supported on silica, alumina or silica-alumina material in an amount in the range of from about 5 to about 50 parts by weight of cobalt per 100 parts by weight of the support material. The catalyst preferably also contains in the range of from about 0.1 to about 5 parts by weight of potassium per 100 parts by weight of support material as a promoter.

The synthesis gas stream flows into and through the reactor 38 at a pressure lower than the pressure within the synthesis gas generator by an amount equal to the pressure drop between the generator 16 and reactor 38. As mentioned above, the temperature within the reactor 38 is in the range of from about 350° F. to about 550° F., and upon contact with the catalyst, hydrogen and carbon monoxide in the synthesis gas stream react to form heavier hydrocarbons and water.

The product stream produced in the reactor 38 exits the reactor by way of a conduit 40 connected thereto which leads the stream to a condensor 42. While flowing through the condensor 42, the heavier hydrocarbons and water contained in the stream are condensed. From the condensor 42, a conduit 44 conducts the stream containing condensed components to a separator 46 wherein the condensed heavier hydrocarbons and water are separated and separately withdrawn. That is, the condensed water is withdrawn from the separator 46 by way of a conduit 48 connected thereto, and the condensed heavier hydrocarbons are withdrawn from the separator 46 by way of a conduit 50 connected thereto.

The residue gas stream from the separator 46 is comprised of nitrogen and unreacted hydrogen, carbon monoxide, light hydrocarbons and carbon dioxide. A conduit 52 connected to the separator 46 leads the residue gas stream from the separator 46 to a second hydrocarbon synthesis reactor 54 containing a fixed bed 56 of the hydrocarbon synthesis catalyst described above. The pressure and temperature of the gas stream flowing through the reactor 54 are maintained at approximately the same levels as the pressure and temperature within the reactor 38 by means of a heater or heat exchanger 58 disposed in the conduit 52 between the separator 46 and reactor 54. While flowing through the reactor 54, additional heavier hydrocarbons are formed from hydrogen and carbon monoxide in the residue gas stream and the resulting product stream exits the reactor 54 by way of a conduit 60 connected thereto. The conduit 60 leads the stream to a condensor 62 wherein heavier hydrocarbons and water contained therein are condensed. From the condensor 62, the stream containing condensed components is conducted to a chiller 66 of a refrigeration unit wherein additional hydrocarbons and water are condensed. The resulting stream is conducted from the chiller 66 to a separator 70 by a conduit 68 connected therebetween. Water is withdrawn from the separator 70 by a conduit 72 connected thereto. The conduit 72 is in turn connected by way of conventional valves and controls (not shown) to the conduit 48, to a drain conduit 31 and to the conduit 32 previously described whereby all or part of the condensed water separated in the separators 46 and 70 is selectively conducted to the synthesis gas generator 16.

The condensed heavier hydrocarbons separated within the separator 70 are withdrawn therefrom by a conduit 74 which connects to the conduit 50 from the separator 46. The conduit 50 leads the heavier hydrocarbons from both the separators 46 and 70 to a conventional fractionation unit 76. A hydrocarbon product stream containing selected components is withdrawn from the fractionation unit 76 by way of a conduit 78 which conducts the product stream to storage or other location. Undesirable light and heavy hydrocarbon fractions produced in the fractionation unit 76 are withdrawn therefrom by conduits 80 and 82, respectively. The conduits 80 and 82 connect to a conduit 84 which conducts the undesirable hydrocarbons to the inlet conduit 12 where they mix with the feed stream of gaseous light hydrocarbons and are recycled.

The residue gas stream from the separator 70 comprising nitrogen and unreacted hydrogen, carbon monoxide, light hydrocarbons and carbon dioxide is withdrawn therefrom by a conduit 86 which leads the residue gas stream to a catalytic combustor 88. The catalytic combustor 88 is comprised of a burner 90 into which the residue gas stream is conducted. A stream of air is conducted to the burner 90 by a conduit 92 connected to the discharge of an air blower 94. The residue gas stream from the separator 70 and the air conducted to the burner 90 are intimately mixed therein, ignited and discharged into a reactor 96 connected to the burner 90. The reactor 96 contains a fixed bed of suitable nobel metal containing catalyst 98, e.g., platinum or palladium, for promoting and catalyzing the oxidation of the oxidizable components in the residue gas stream. As a result of such oxidation an oxidation product stream comprising carbon dioxide, water vapor and nitrogen is produced and withdrawn from the combustor 88 by a conduit 100 connected thereto. The conduit 100 leads the product stream to a conventional carbon dioxide removal unit 102. Carbon dioxide and water are removed from the stream by the carbon dioxide removal unit 102 thereby producing a relatively pure nitrogen product stream which is conducted from the unit 102 by a conduit 104 to a location of sale, storage or further processing.

The carbon dioxide removed by the unit 102 is withdrawn therefrom by a conduit 106 which leads the carbon dioxide to a compressor 108. The discharge of the compressor 108 is connected by way of conventional valves nnd controls (not shown) to a vent 35 and to the conduit 34 previously described whereby all or part of the carbon dioxide is selectively introduced into the synthesis gas generator 16.

As previously described, the flow rates of tee water conducted to the synthesis gas generator 16 by way of the conduit 32 and carbon dioxide conducted thereto by way of the conduit 34 are varied as is necessary to control the ratio of hydrogen to carbon monoxide in the synthesis gas stream produced to as close to 2:1 as possible. This in turn improves the efficiency of the hydrocarbon synthesis reactions carried out in the reactors 38 and 54. Further, the use of air in the synthesis gas generator as the source of oxygen for the partial oxidation reaction carried out therein produces nitrogen in the synthesis gas stream. Such nitrogen acts as a diluent in the hydrocarbon synthesis reactors 38 and 54 which prevents hot spots on the catalyst and further increases the efficiency of the hydrocarbon synthesis reactions. That nitrogen together with the additional nitrogen produced in the catalytic combustor 88, after carbon dioxide removal, form a relatively pure nitrogen product stream. In addition, the recycling of all or part of the removed carbon dioxide provides additional carbon for producing heavier hydrocarbons and increases overall process efficiency.

In order to further illustrate the process and apparatus of the present invention, the following example is given.

EXAMPLE

A 1 million scf/day natural gas stream having a specific gravity of 0.55 and a calorific value of 1000 BTU/scf at a pressure of 100 psig and a temperature of 60° F. is conducted to the heat exchanger 10 by way of the conduit 12. While flowing through the heat exchanger 10, the natural gas stream is heated to a temperature of 750° F. A 7963 pounds/hour stream of air is heated to a temperature of 750° F. while flowing through the heat exchanger 22, and the natural gas stream and air are reacted by combustion in the synthesis gas generator 16 at a temperature of 2500° F.

The synthesis gas generator 16 contains a fixed bed of catalyst comprised of nickle and/or chrome oxide containing catalyst. A 360 pounds/hour stream of water is introduced into the reactor 28 by way of the conduit 32. A 220 pounds/hour stream of carbon dioxide is introduced into the reactor 28 by way of the conduit 34, and the autothermal reforming reactions combined with the reaction of carbon dioxide with unreacted light hydrocarbons within the generator 16 produce a 9346 pounds/hour stream of synthesis gas containing hydrogen and carbon monoxide at a ratio of about 2:1.

The synthesis gas produced in the generator 16 is conducted to the hydrocarbon synthesis reactor 38 at a pressure of 85 psig and a temperature of 425° F. The hydrocarbon synthesis reaction produces a product stream which results in 774 pounds/hour of hydrocarbons being condensed at a temperature of $-10°$ F., separated in the separator 46 and withdrawn therefrom. A 7058 pounds/hour stream of residue gas is withdrawn from the separator 46, at a pressure of 75 psig, heated to a temperature of 450° F. and introduced into the hydrocarbon synthesis reactor 54. Unreacted hydrogen and carbon monoxide contained in the residue gas stream are converted to hydrocarbons within the reactor 54 resulting in 345 pounds/hour of additional heavier hydrocarbons being condensed at a final temperature of $-10°$ F. and withdrawn from the separator 70 by way of the conduit 74.

A 1119 pounds/hour stream of hydrocarbons is conducted to the fractionation unit 76, and a 183 gallons/hour hydrocarbon product stream having a specific gravity of 0.72 is withdrawn from the fractionation unit by way of the conduit 78. 22 pounds/hour of undesirable light and heavy hydrocarbons are recycled to the feed stream conduit 12 by way of the conduit 84.

A 6227 pounds/hour residue gas stream is withdrawn from the separator 70 and subjected to catalytic combustion with 5800 pounds/hour of air in the catalytic combustor 88. A 10,752 pounds/hour stream is conducted to the carbon dioxide removal unit 102 wherein carbon dioxide is separated producing a 9548 pounds/hour high purity nitrogen product stream. 220 pounds/hour of removed carbon dioxide are recycled from the carbon dioxide removal unit 102 to the synthesis gas generator 16. 984 pounds/hour of carbon dioxide are vented.

Both the water conducted to the synthesis gas generator 16 by way of the conduit 32 and carbon dioxide conducted thereto by way of the conduit 34 are varied in accordance with changes in the hydrogen to carbon monoxide ratio in the produced synthesis gas to maintain such ratio at about 2:1.

Thus, the present invention is well adapted to carry out the objects and attain the ends and advantages mentioned as well as those inherent therein. While numerous changes in the arrangement of steps and components can be made by those skilled in the art, such changes are encompassed within the spirit of this invention as defined by the appended claims.

What is claimed is:

1. A process for the production of heavier hydrocarbons from one or more gaseous light hydrocarbons comprising the steps of:
  (a) reacting said gaseous light hydrocarbons with air to partially oxidize a portion thereof and produce a gas stream comprising unreacted light hydrocarbons, hydrogen, carbon monoxide and nitrogen;
  (b) reacting the gas stream from step (a) with steam and carbon dioxide in the presence of a steam reforming catalyst to convert a substantial portion of the unreacted light hydrocarbons therein to additional hydrogen and carbon monoxide and to produce a synthesis gas stream containing hydrogen and carbon monoxide in desired proportion;
  (c) reacting the synthesis gas stream from step (b) in the presence of a hydrocarbon synthesis catalyst containing cobalt to form heavier hydrocarbons and water from hydrogen and carbon monoxide in said stream;
  (d) separating heavier hydrocarbons and water from the product stream of step (c) leaving a residue gas stream comprised of unreacted hydrogen and carbon monoxide, light hydrocarbons, carbon dioxide and nitrogen;
  (e) subjecting the residue gas stream from step (d) to catalytic combustion with additional air to form a product stream comprising carbon dioxide, water vapor and nitrogen;
  (f) separating carbon dioxide from the product stream of step (e); and
  (g) utilizing at least a portion of the carbon dioxide separated in step (f) for carrying out step (b).

2. The process of claim 1 wherein steps (a) and (b) are each carried out at a pressure in the range of from about atmospheric to about 100 psig and a temperature in the range of from about 1500° F. to about 3500° F.

3. The process of claim 2 wherein step (c) is carried out at substantially the same pressure as steps (a) and (b) and at a temperature in the range of from about 350° F. to about 550° F.

4. The process of claim 1 wherein said hydrocarbon synthesis catalyst comprises from about 5 to about 50 parts by weight cobalt per 100 parts by weight of silica, alumina or silica-alumina support.

5. The process of claim 4 wherein said catalyst is further characterized to include from about 0.1 to about 5 parts by weight of potassium per 100 parts by weight of said support.

6. The process of claim 1 wherein the rates of steam and carbon dioxide utilized in carrying out step (b) are varied to control the molar ratio of hydrogen to carbon monoxide in the synthesis gas stream produced at substantially 2:1.

7. The process of claim 1 wherein the catalytic combustion of step (e) is carried out at a pressure in the range of from about atmospheric to about 100 psig and a temperature in the range of from about 400° F. to about 1000° F.

8. The process of claim 1 wherein step (d) comprises:
  cooling said product stream of step (c) whereby said heavier hydrocarbons and water are condensed; and
  withdrawing said condensed heavier hydrocarbons and water from the resulting residue gas stream.

9. The process of claim 8 which is further characterized to include the steps of:
  separating said heavier hydrocarbons from said water; and
  utilizing at least a portion of said separated water to form steam used in step (b).

10. The process of claim 9 which is further characterized to include the steps of:
  subjecting said separated hydrocarbons to fractionation to produce a product stream containing selected hydrocarbon components and a residue hydrocarbon stream; and
  recycling said residue hydrocarbon stream to step (a).

11. A process for the production of heavier hydrocarbons from one or more gaseous light hydrocarbons comprising the steps of:
  (a) reacting said gaseous light hydrocarbons with air to partially oxidize a portion thereof and produce a gas stream comprising unreacted light hydrocarbons, hydrogen, carbon monoxide and nitrogen;
  (b) reacting the gas stream from step (a) with steam and carbon dioxide in the presence of a steam reforming catalyst containing nickle to convert a substantial portion of the unreacted light hydrocarbons therein to additional hydrogen and carbon monoxide to produce a synthesis gas stream containing hydrogen and carbon monoxide in a molar ratio of about 2:1;
  (c) reacting the synthesis gas stream from step (b) in the presence of a hydrocarbon synthesis catalyst containing cobalt to form heavier hydrocarbons and water from hydrogen and carbon monoxide in said stream;
  (d) cooling the product stream of step (c) whereby said heavier hydrocarbons and water are condensed;
  (e) withdrawing said condensed heavier hydrocarbons and water from the resulting residue gas stream;
  (f) separating said condensed heavier hydrocarbons from said condensed water;
  (g) utilizing at least a portion of said separated water to form steam used in step (b);
  (h) subjecting the residue gas stream from step (e) to catalytic combustion with additional air to form a product stream comprising carbon dioxide, water vapor and nitrogen;
  (i) separating carhon dioxide from the product stream of step (h);
  (j) utilizing at least a portion of the carbon dioxide separated in step (i) in carrying out step (b); and
  (k) varying the rates of water utilized in accordance with step (g) and carbon dioxide utilized in accordance with step (j) for carrying out step (b) to thereby control the molar ratio of hydrogen to carbon monoxide in the synthesis gas stream produced in step (b) at about 2:1.

12. The process of claim 11 wherein steps (a) and (b) are each carried out at a pressure in the range of from about atmospheric to about 100 psig and a temperature in the range of from about 1500° F. to about 3500° F.

13. The process of claim 12 wherein step (c) is carried out at substantially the same pressure as steps (a) and (b) and at a temperature in the range of from about 350° F. to about 550° F.

14. The process of claim 11 wherein said hydrocarbon synthesis catalyst comprises from about 5 to about 50 parts by weight cobalt per 100 parts by wweight of silica, alumina or silica-alumina support.

15. The process of claim 14 wherein said catalyst is further characterized to include from about 0.1 to about 5 parts by weight of potassium per 100 parts by weight of said support.

16. The process of claim 11 wherein the catalytic combustion of step (e) is carried out at a pressure in the range of from about atmospheric to about 100 psig and a temperature in the range of from about 400° F. to about 1000° F.

17. The process of claim 11 which is further characterized to include the steps of:
subjecting said separated condensed heavier hydrocarbons from step (f) to fractionation to produce a hydrocarbon product stream containing selected hydrocarbon components and a residue hydrocarbon stream; and
recycling said residue hydrocarbon stream to step (a).

18. The process of claim 11 which is further characterized to include the step of exchanging heat between said gaseous light hydrocarbons prior to carrying out step (a) with the synthesis gas stream produced in step (b).

19. The process of claim 18 wherein steps (a) and (b) are carried out in a single synthesis gas generation vessel.

20. The process of claim 11 which is further characterized to include the steps of:
prior to carrying out step (h), reacting the residue gas stream produced in step (e) a second time in the presence of a hydrocarbon synthesis catalyst containing cobalt to form additional heavier hydrocarbons and water from unreacted hydrogen and carbon monoxide contained in said residue gas stream;
cooling the resulting product stream whereby said additional heavier hydrocarbons and water are condensed; and
withdrawing said condensed heavier hydrocarbons and water from the resulting residue gas stream.

* * * * *

UNITED STATES PATENT AND TRADEMARK OFFICE
CERTIFICATE OF CORRECTION

PATENT NO. : 4,833,170
DATED : May 23, 1989
INVENTOR(S) : Kenneth L. Agee

It is certified that error appears in the above-identified patent and that said Letters Patent is hereby corrected as shown below:

Column 1, line 27, delete the equation reading:
"$2H_2 + CO \xrightarrow{catalyst} -(CH_2- + H_2O$" and insert
--$2H_2 + CO \xrightarrow{catalyst} -(CH_2)- + H_2O$ --;

Column 1, line 44, after "and" and before "cata-" insert --a--;

Column 2, line 24, delete "hydrocabbon" and substitute --hydrocarbon-- therefor;

Column 2, line 51, change "iight" to --light--;

Column 4, line 48, delete "airccompressor" and substitute the words --air compressor-- therefor;

Column 5, line 52, change "35" to --23--;

Column 6, line 44, after "unit" and before "wherein" insert --by a conduit 64--;

Column 7, line 34, delete "nnd" and substitute the word --and-- therefor;

Column 7, line 38, change "tee" to --the--;

Column 10, line 45 [claim 11, (i)], delete the word "carhon" and substitute the word --carbon-- therefor; and

UNITED STATES PATENT AND TRADEMARK OFFICE
CERTIFICATE OF CORRECTION

PATENT NO. : 4,833,170

DATED : May 23, 1989

INVENTOR(S) : Kenneth L. Agee

It is certified that error appears in the above-identified patent and that said Letters Patent is hereby corrected as shown below:

Column 10, line 65, (claim 14), change "wweight" to -- weight --.

Signed and Sealed this

Sixteenth Day of January, 1990

*Attest:*

JEFFREY M. SAMUELS

*Attesting Officer*     Acting Commissioner of Patents and Trademarks